United States Patent
Barrile-Josephson et al.

(10) Patent No.: US 7,922,736 B2
(45) Date of Patent: Apr. 12, 2011

(54) STEPPED MICROKERATOME BLADE HOLDER

(75) Inventors: Craig A. Barrile-Josephson, Ontario, NY (US); Peter J. Halecki, Rochester, NY (US); Michael H. Dobner, Honeoye Falls, NY (US)

(73) Assignee: Technolas Perfect Vision GmbH (DE)

( * ) Notice: Subject to any disclaimer, the term of this patent is extended or adjusted under 35 U.S.C. 154(b) by 305 days.

(21) Appl. No.: 11/729,465

(22) Filed: Mar. 29, 2007

(65) Prior Publication Data

US 2008/0243155 A1  Oct. 2, 2008

(51) Int. Cl.
 *A61F 9/00* (2006.01)
(52) U.S. Cl. ........................................................ 606/166
(58) Field of Classification Search .................. 606/166, 606/167, 161, 172, 169, 170; 403/190, 168
 See application file for complete search history.

(56) References Cited

U.S. PATENT DOCUMENTS

| | | | |
|---|---|---|---|
| 5,342,378 A | * | 8/1994 | Giraud et al. ................. 606/166 |
| 6,051,009 A | | 4/2000 | Hellenkamp |
| 6,165,189 A | | 12/2000 | Ziemer ......................... 606/166 |
| 2004/0236358 A1 | | 11/2004 | Barrile-Josephson et al. ................................. 606/166 |

FOREIGN PATENT DOCUMENTS

| EP | 1 752 120 | 2/2007 |
|---|---|---|
| WO | WO 02/17834 | 3/2002 |

OTHER PUBLICATIONS

Geoffrey Boothroyd, Peter Dewhurst, Winston Knight, Product Design for Manufacture and Assembly, 1994, Marcel Dekker, Inc., pp. 65 and 67.*

International Search Report (PCTISA/210) and Written Opinion (PCT/ISA/237) mailed on Jul. 11, 2008.

* cited by examiner

*Primary Examiner* — (Jackie) Tan-Uyen T Ho
*Assistant Examiner* — Tuan V Nguyen
(74) *Attorney, Agent, or Firm* — Harness, Dickey & Pierce, P.L.C.

(57) ABSTRACT

A blade holder 16 includes a bottom surface 18 for attachment to a blade 30. A top surface 20 interfaces with a drive-pin 32 of a microkeratome 38. A drive slot 22 is formed in the top surface 20 for engagement with the drive-pin 32 for allowing oscillation of the blade holder 16. A plurality of steps 24 are formed in the top surface 20, and rise from the drive slot 22 toward at least one side 26 of the blade holder 16.

7 Claims, 5 Drawing Sheets

STEPPED MICROKERATOME BLADE HOLDER

BACKGROUND OF THE INVENTION

1. Field of the Invention

The present invention is related to microkeratome blade holders and blade assemblies for use in microkeratomes. More specifically, the present invention is directed to a stepped blade holder for more easily assuring that a microkeratome blade assembly is properly loaded into a microkeratome before use during surgery.

2. Description of Related Art

Microkeratomes and their associated blade assemblies and blade holders are well-known in the art. Microkeratomes include the Hansatome™ and the XP Microkeratome™ both, of which are sold by Bausch & Lomb Incorporated, the assignee of the present invention. U.S. Pat. No. 6,051,009 entitled Automatic Surgical Device for Cutting a Cornea and a Cutting Blade Assembly and Control Assembly, and U.S. Patent Publication No. 2004/0236358 entitled Bar-Link Drive System for a Microkeratome both describe microkeratomes and related microkeratome blade assemblies and both are incorporated in their entirety herein.

Blade holders are typically a structure attached to a metal, ceramic, or plastic cutting blade. The blade holder and the attached cutting blade form a blade assembly that fits within mating structure of the microkeratome. The blade holder typically cooperates with an eccentric drive-pin via a drive slot formed in the blade holder. The drive-pin, properly positioned within the drive slot, then oscillates the blade assembly during operation of the microkeratome, as it is passed across the cornea of a patient's eye during surgery, to form a corneal flap, such as for LASIK surgery. The oscillation of the blade during movement of the blade assembly across the cornea of a patient's eye is important in order to effectively and efficiently cut the cornea of the patient's eye; therefore, the seating or placement of the eccentric drive-pin in the drive slot of the blade holder is particularly important to ensure that the blade is oscillated.

Prior art blade assemblies described in the above-referenced patents and in other known microkeratomes, are effective in oscillating the blade assembly and safely and efficiently cutting a cornea during surgery, if the microkeratome blade assembly is properly placed within the microkeratome and the drive slot is properly engaged with the drive-pin of the microkeratome.

In rare circumstances, the blade assembly may not be properly loaded into the microkeratome, and a user through inattention or some other mistake may not fully place the blade assembly within the microkeratome. This may prevent the drive-pin from being engaged with the drive slot of the blade holder. If this occurs, serious complications could result and an improper flap may be formed or other damage not intended could be done to a patient's cornea.

U.S. Pat. No. 6,165,189 entitled Microkeratome for Performing LASIK Surgery discloses a conical counter sink in an upper surface of a sled. This counter sink may allow for easier engagement with an eccentric drive-pin but the sled must still be placed well into the microkeratome before the counter sink would be effective.

Therefore, there is a need for an improved blade holder and blade assembly that will ensure that the blade assembly becomes engaged with the drive-pin properly, so that the safety and effectiveness of the microkeratome during surgery may be increased.

DETAILED DESCRIPTION OF THE PREFERRED EMBODIMENTS

Figure 1:
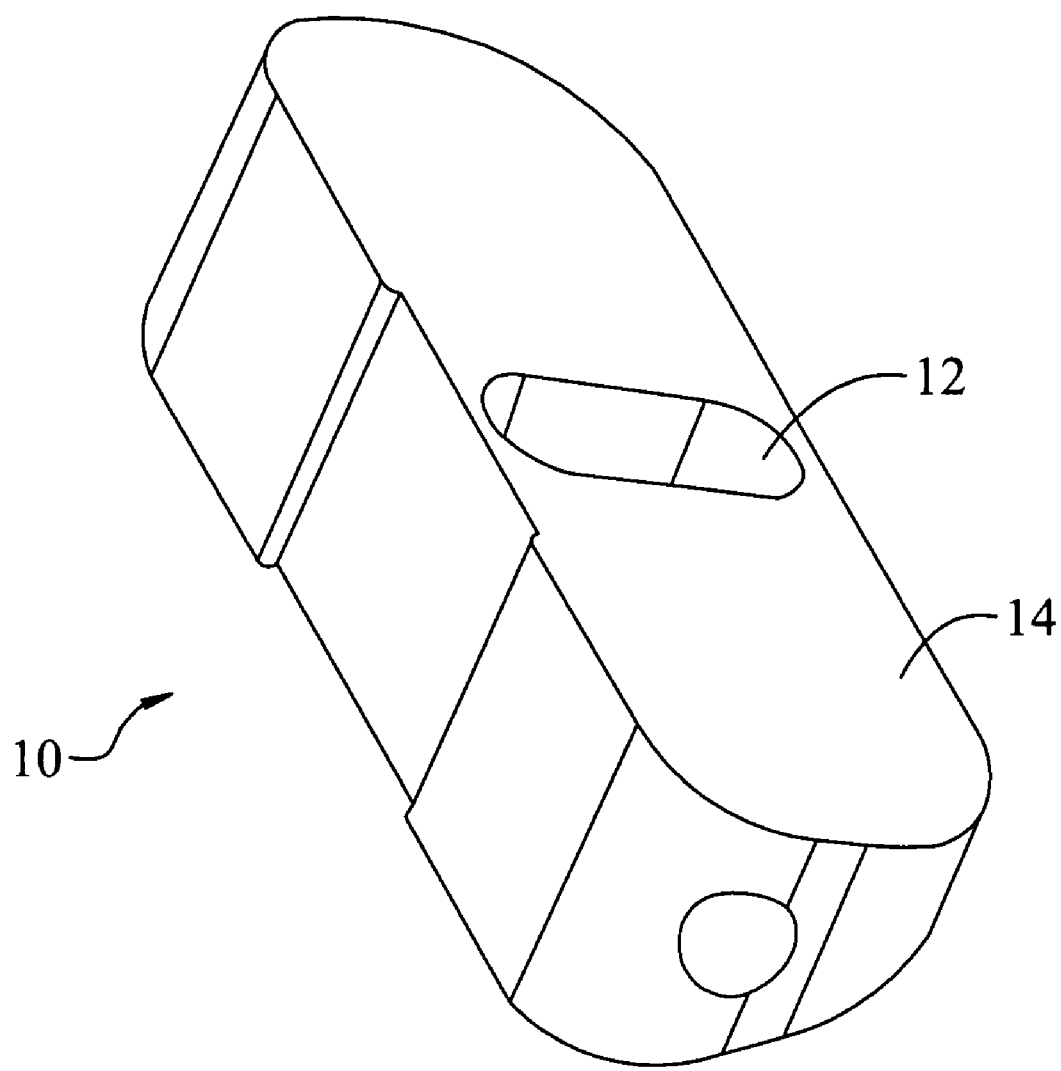
FIG. 1 is a perspective view of a prior art blade holder.
Figure 2:
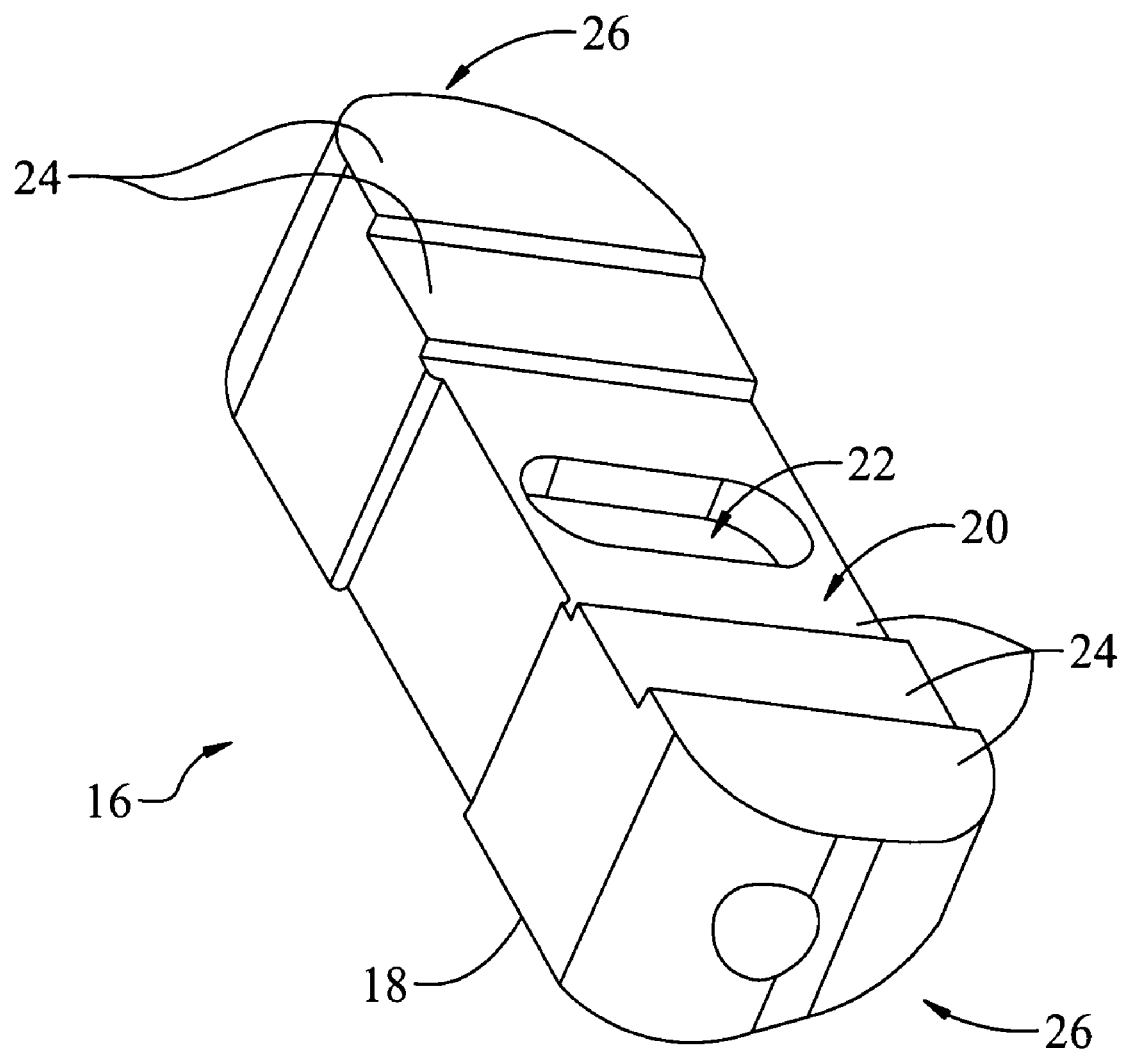
FIG. 2 is a perspective view of a blade holder in accordance with the present invention.

FIG. 1 shows a perspective view of a prior art blade holder 10 having a drive slot 12 and an essentially top surface 14. The present invention, an example of which is shown in FIG. 2, improves on the prior art of FIG. 1 by forming a series of steps on a top surface. These steps cooperate with the rotation of a drive-pin to ensure that as the eccentric drive-pin of the microkeratome is rotated, the steps cooperate with the drive-pin to ensure that the drive-pin engages with the drive slot of a blade holder.

FIG. 2 shows a perspective view of a blade holder 16 for attachment to a microkeratome blade, in accordance with the present invention. Blade holder 16 includes a bottom surface 18. Bottom surface 18 is shown at the line 18, but cannot be seen in the perspective view. A top surface, shown generally at 20, in use, interfaces with the drive-pin of a microkeratome. A drive slot 22 is formed in top surface 20 and is for engagement with the drive-pin for allowing oscillation of blade holder 16. A plurality of steps 24 are formed in the top surface 20, and rise from the drive slot 22 toward at least one side, shown generally at 26, of the blade holder 16.

Preferably, a width of each step 24 is less than a diameter of rotation of the drive-pin for ensuring that the drive-pin is directed toward the drive slot 22. This relationship between the width of the step and the rotation of the drive-pin is shown more explicitly below with regard to FIG. 4. As will become more apparent with regard to the discussion relating to FIG. 4, the formation of the three steps 24 in blade holder 16 ensures that the drive-pin will be engaged in the drive slot 22 within three revolutions of the drive-pin after the drive-pin contacts the top surface 20.

In order for the steps of blade holder 16 to properly work with the microkeratome, a plurality of steps should be formed toward at least one side of the blade holder; but depending on the design of the microkeratome, it may be desirable for the steps to be formed from the drive slot 22 toward opposing sides of the blade holder 16, as shown in FIG. 2. Such a symmetrical step configuration as shown in FIG. 2, is particularly desirable in microkeratomes designed to allow for blade assembly insertion from either of opposing sides. Other microkeratomes may be designed to only allow blade assembly insertion from one side and therefore, it would only require steps to be formed on one side of the blade holder. In addition, more or fewer than the three steps formed from the drive slot toward the sides of blade holder 16 may be formed, depending on the diameter of rotation of the drive-pin to be used in conjunction with the blade assembly.

Figure 3:
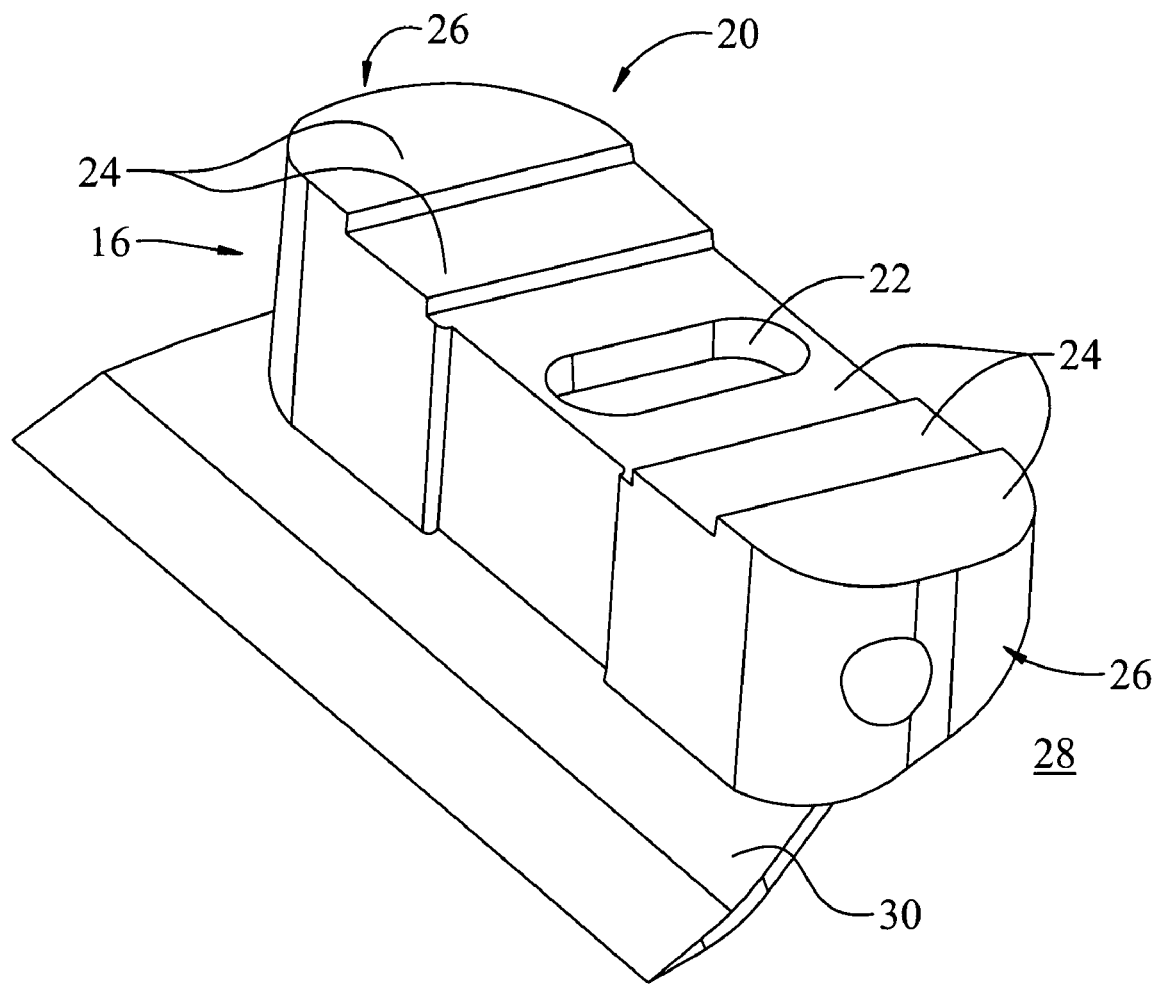
FIG. 3 is a perspective view of a microkeratome cutting blade assembly in accordance with the present invention.

FIG. 3 shows a microkeratome blade assembly 28 with a cutting blade 30 attached to blade holder 16. Bottom surface 18 is attached to the blade 30. Top surface 20 interfaces with a drive-pin of a microkeratome, as described in detail below. A drive slot 22 is formed in the top surface 20 for engagement with the drive-pin. As in FIG. 2, a plurality of steps are formed in the top surface 20 and rise from the drive slot 22 towards opposing sides 26 of the blade holder 16.

Figure 4:
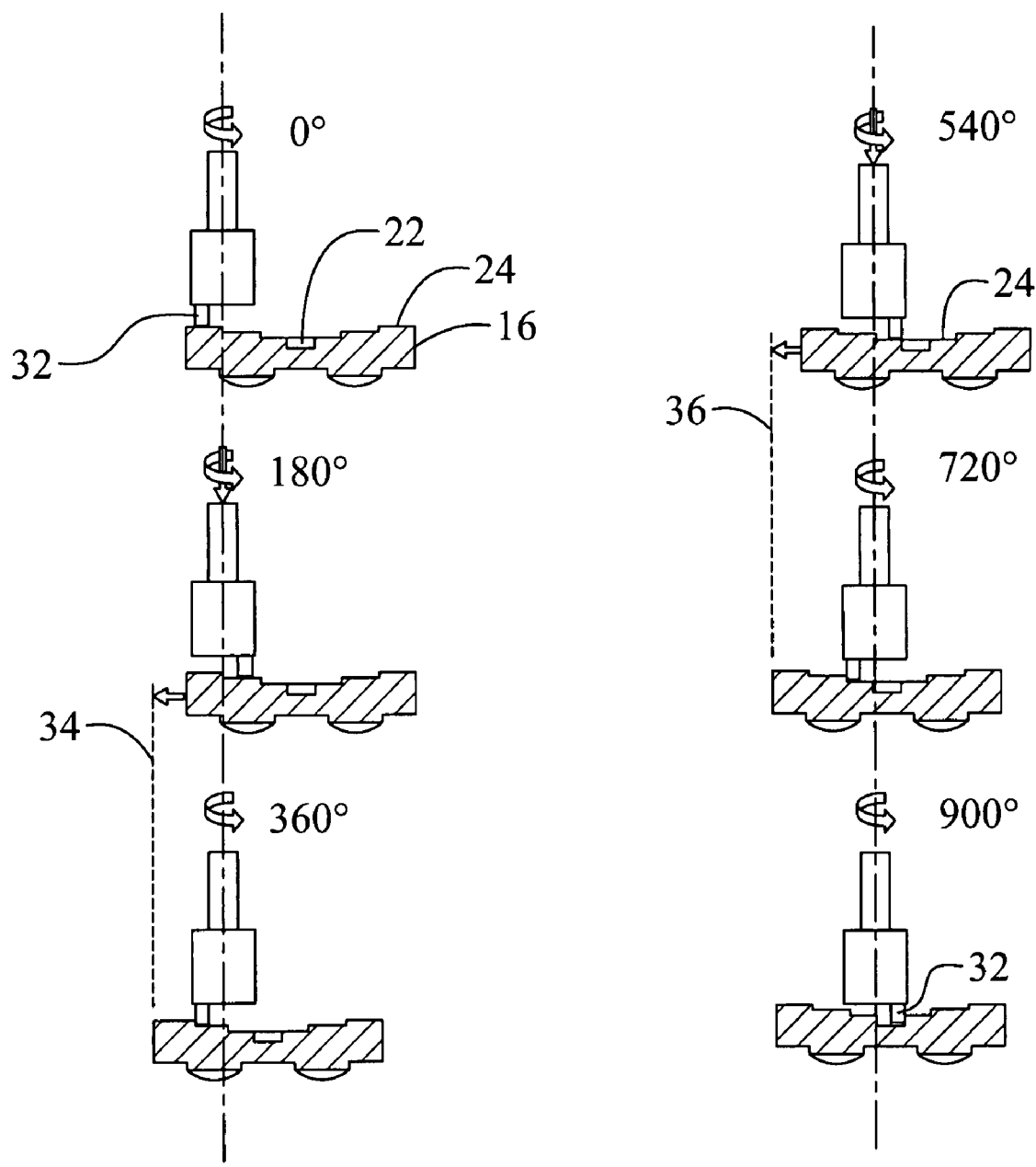
FIG. 4 is a series of views showing the rotation of an eccentric drive-pin of a microkeratome with a blade holder in accordance with the present invention.

FIG. 4 shows a series of drawings depicting how the inventive blade holder 16 cooperates with an eccentric drive-pin 32, to ensure that drive-pin 32 is engaged in drive slot 22 within three revolutions. The series of drawings of FIG. 4 depict the drive-pin 32 and blade holder 16; though in operation those skilled in the art will appreciate, the drive-pin 32 is contained within the microkeratome and blade holder 16 is attached to a cutting blade 30, which has at least partially been loaded into a microkeratome. In the example used, blade holder 16 is only partially engaged within a microkeratome, such as shown in the drawing at 0°. When eccentric pin 32 starts to rotate and reaches 180°, because pin 32 is typically spring loaded and the width of steps 24 are each less than the diameter of revolution of drive-pin 32, between 180° and 360° of revolution, blade holder 16 will be pulled within the microkeratome a distance, as indicated by dashed line 34. As drive-pin 32 continues to rotate past 360°, pin 32 will then engage with the lowest step 24, as indicated at 540°. Between 540° and 720° blade holder 16 will be further pulled within the microkeratome, as indicated by dashed line 36. Finally by 900°, pin 32 will become engaged with drive slot 22 of blade holder 16, thus ensuring proper oscillation of the blade assembly and a safe and effective cut of a patient's cornea during a procedure.

As indicated above, some prior art has shown the use of conical counter sinks with a drive slot. These conical counter sinks provide a larger area in which to engage the drive-pin, to allow the drive-pin to more quickly become engaged with the drive slot. However, the present invention is distinctly different from such a conical counter sink. The conical counter sinks do not span virtually the entire width from the drive slot to at least one side of the blade holder, as the present invention does. Therefore, the prior art requires the blade holder or blade assembly to be almost completely inserted within the microkeratome to ensure that the drive-pin is engaged with the counter sink hole. In addition, the present inventors found that simply providing an inclined surface from the side of a blade holder to the drive slot would not ensure that the drive-pin engages with the drive slot. Because the incline is so slight, the drive-pin can actually simply spin on an inclined top surface of a blade holder. Therefore, the steps 24 of the present invention ensure that the drive-pin engages with the side of each step in order to effectively and quickly direct the drive-pin towards the drive slot, and engage the blade holder with the drive-pin within three revolutions of the drive-pin. Of course, depending on the design of the drive-pin and the blade holder and blade slot, more or fewer than three steps 24 may be desirable.

Figure 5:
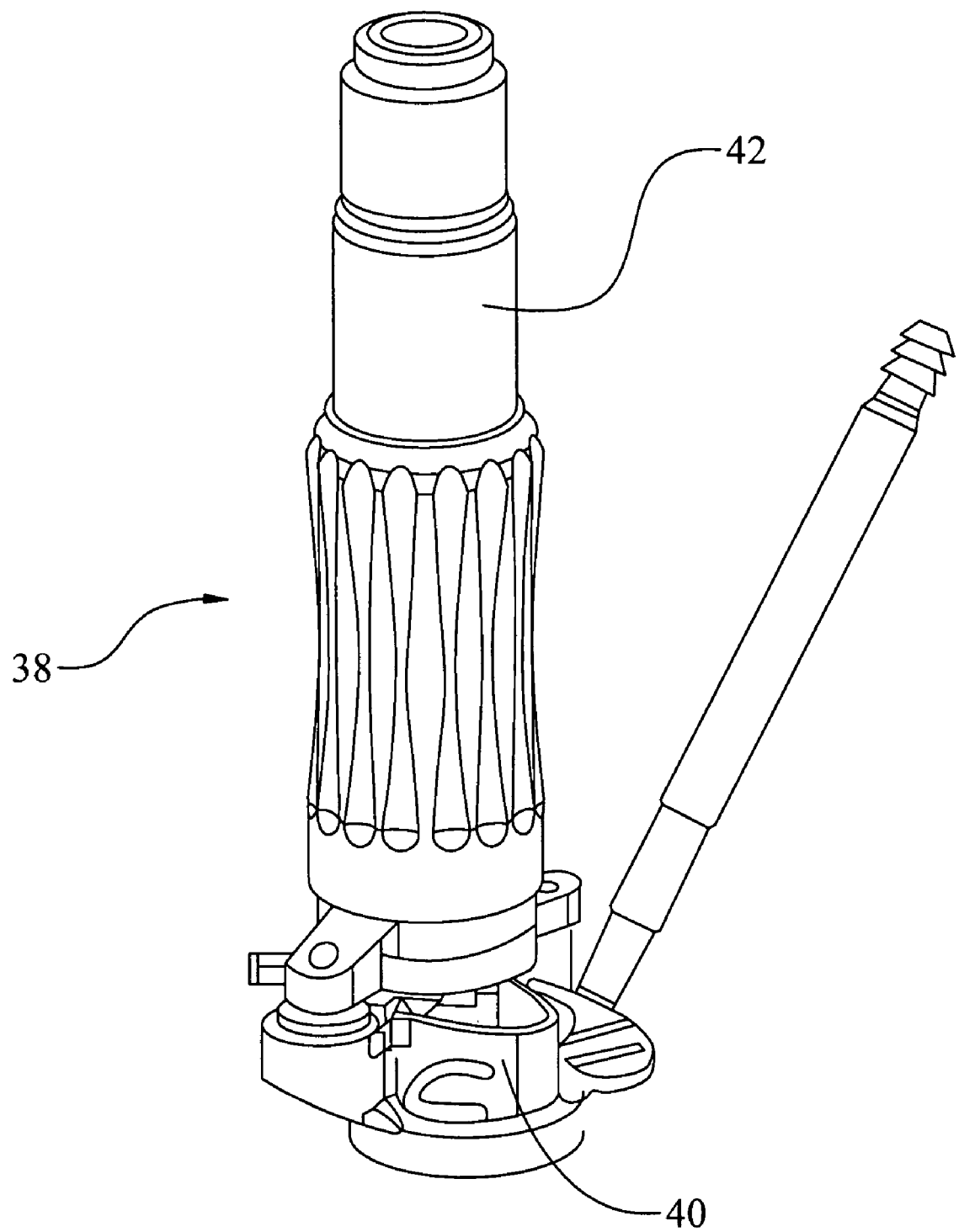
FIG. 5 shows a microkeratome system in accordance with the present invention.

FIG. 5 shows a microkeratome system 38, in accordance with the present invention. Microkeratome 38 is similar to the microkeratome fully described and incorporated by reference above with respect to U.S. Patent Publication No. 2004/0236358. System 38 includes a drive-pin 32 which extends down within head assembly 40, but is not seen in this view. Cutting blade assembly 28 is also held within head assembly 40. As described above, cutting blade assembly 28 includes a cutting blade 30 and blade holder 16 attached to the cutting blade. The blade holder 16 includes a bottom surface 18 attached to the blade 30, a top surface 20 for interfacing with the drive-pin 32, and a drive slot 22 formed in the top surface 20 for engagement with the drive-pin for oscillating the cutting blade assembly 28. As described in detail above, a plurality of steps 24 are formed in the top surface 20 and rise from the drive slot 22 toward at least one side 26 of the blade holder 16. A motor for rotating the drive-pin 32 is contained within the housing 42 of FIG. 5.

In operation, the microkeratome system 38 will be energized and will rotate the drive-pin many times before engagement with the patient's eye and therefore, by ensuring that the blade holder is engaged with the drive-pin within three revolutions of the drive-pin, safe operation of the microkeratome 38 can be assured.

As with prior art blade holders, blade holder 16 may be formed of any suitable material and may be molded or machined, depending on the cost and design requirements.

What is claimed:

1. A blade holder for attachment to a microkeratome blade comprising:
    a bottom surface for attachment to the blade;
    a top surface for interfacing with a drive-pin of a microkeratome;
    a drive slot formed in the top surface for engagement with the drive-pin for allowing oscillation of the blade holder;
    a plurality of steps formed in the top surface and rising from the drive slot toward at least one side of the blade holder; and
    wherein a width of each step is less than a diameter of rotation of the drive-pin for ensuring that the drive-pin is directed toward the drive slot.

2. The blade holder of claim 1, wherein the step widths ensure that the drive-pin will be engaged in the drive slot within three revolutions of the drive-pin after the drive-pin contacts the top surface.

3. The blade holder of claim 1, wherein three steps are formed from the drive slot towards at least one side of the blade holder.

4. A microkeratome cutting blade assembly comprising:
    a cutting blade; and
    a blade holder attached to the cutting blade, the blade holder including:
        a bottom surface attached to the blade;
        a top surface for interfacing with a drive-pin of a microkeratome;
        a drive slot formed in the top surface for engagement with the drive-pin;
        a plurality of steps forming the top surface and rising from the drive slot toward opposing sides of the blade holder; wherein a width of each step ensure that the drive-pin will be engaged in the drive slot within three revolutions of the drive-pin after the drive-pin contacts the top surface; and
    wherein three steps are formed from the drive slot towards each opposing side of the blade holder.

5. A microkeratome system comprising:
    a drive-pin having a diameter of revolution;
    a cutting blade assembly held within the microkeratome including:
        a cutting blade; and
        a blade holder attached to the cutting blade, the blade holder including:
            a bottom surface attached to the blade;
            a top surface for interfacing with the drive-pin;
            a drive slot formed in the top surface for engagement with the drive-pin for oscillating the cutting blade assembly; and
            a plurality of steps formed in the top surface and rising from the drive slot toward at least one side of the blade holder;
    a motor for rotating the drive-pin, and
    wherein a width of each step is less than a diameter of rotation of the drive-pin for ensuring that the drive-pin is directed toward the drive slot.

6. The system of claim 5, wherein the step widths ensure that the drive-pin will be engaged in the drive slot within three revolutions of the drive-pin after the drive-pin contacts the top surface.

7. The system of claim 5, wherein three steps are formed from the drive slot towards the at least one side of the blade holder.

* * * * *